(12) United States Patent
Burkamp et al.

(10) Patent No.: US 8,203,004 B2
(45) Date of Patent: Jun. 19, 2012

(54) TETRAHYDROINDOLE DERIVATIVES FOR TREATMENT OF ALZHEIMER'S DISEASE

(75) Inventors: Frank Burkamp, Scheelevaegen (SE); Graham David Checksfield, Canterbury (GB); Stephen Robert Fletcher, Bishops Stortford (GB); Stephen John Lewis, East Barnet (GB); Edward Giles Mciver, London (GB); Paul Joseph Oakley, Horsham (GB); Martin Richard Teall, Bishops Stortford (GB)

(73) Assignee: Merck, Sharp & Dohme Limited, Hoddesdon, Herfordshire (GB)

( * ) Notice: Subject to any disclaimer, the term of this patent is extended or adjusted under 35 U.S.C. 154(b) by 371 days.

(21) Appl. No.: 12/084,814

(22) PCT Filed: Nov. 3, 2006

(86) PCT No.: PCT/GB2006/050368
§ 371 (c)(1),
(2), (4) Date: Aug. 25, 2009

(87) PCT Pub. No.: WO2007/054739
PCT Pub. Date: May 18, 2007

(65) Prior Publication Data
US 2010/0016308 A1    Jan. 21, 2010

(30) Foreign Application Priority Data
Nov. 10, 2005 (GB) .................... 0522908.3

(51) Int. Cl.
*C07D 209/02* (2006.01)
*C07D 209/52* (2006.01)
(52) U.S. Cl. .................................. 548/452
(58) Field of Classification Search ......... 548/360.1, 548/452
See application file for complete search history.

(56) References Cited

FOREIGN PATENT DOCUMENTS

| WO | WO 98/04527 | 2/1998 |
|---|---|---|
| WO | WO 2005/013985 | 2/2005 |
| WO | WO 2005/054193 | 6/2005 |
| WO | WO 2005/108362 | 11/2005 |

OTHER PUBLICATIONS

Vippagunta, et al. Advanced Drug Delivery Reviews 48 (2001) 3-26.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Dementia [online], [retrieved on May 24, 2007]. Retrieved from the Internet, URL; http:llen.wikipedia.orglwikilDementia>.*

* cited by examiner

*Primary Examiner* — Shawquia Young
(74) *Attorney, Agent, or Firm* — Susan L. Hess; Gerard M. Devlin

(57) ABSTRACT

Tetrahydroindole derivatives of formula (I): are disclosed. These compounds modulate the activity of gamma-secretase and hence find use in treatment or prevention of Alzheimer's disease.

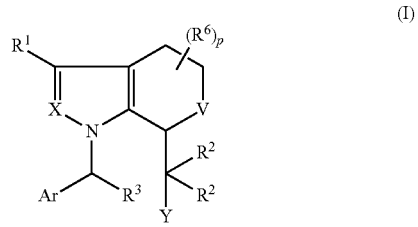

6 Claims, No Drawings

TETRAHYDROINDOLE DERIVATIVES FOR TREATMENT OF ALZHEIMER'S DISEASE

RELATED APPLICATION DATA

This is a National filing under 35 U.S.C. 371 of PCT/GB2006/050368, filed Nov. 3, 2006, which claims priority under 35 U.S.C. 119(a) and 365(b) to GB0522908.3, filed Nov. 10, 2005.

This invention relates to methods and materials for use in therapeutic treatment of the human body. In particular, it provides materials for treating diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4$^{th}$ ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase. Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by β-secretase. For the sake of convenience, expressions such as "Aβ(1-40)" and "Aβ(1-42)" as used herein are inclusive of such N-terminal truncated variants. After secretion into the extracellular medium, Aβ forms initially-soluble aggregates which are widely believed to be the key neurotoxic agents in AD (see Gong et al, *PNAS*, 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral haemorrhage with amyloidosis, Dutch-type (HCHWA-D), multi-infarct dementia, dementia pugilistica and Down syndrome.

Various interventions in the plaque-forming process have been proposed as therapeutic treatments for AD (see, for example, Hardy and Selkoe, *Science*, 297 (2002), 353-6). One such method of treatment that has been proposed is that of blocking or attenuating the production of Aβ for example by inhibition of β- or γ-secretase. It has also been reported that inhibition of glycogen synthase kinase-3 (GSK-3), in particular inhibition of GSK-3α, can block the production of Aβ (see Phiel et al, *Nature*, 423 (2003), 435-9). Other proposed methods of treatment include administering a compound which blocks the aggregation of Aβ, and administering an antibody which selectively binds to Aβ.

However, recent reports (Pearson and Peers, *J. Physiol.*, 575.1 (2006), 5-10) suggest that Aβ may exert important physiological effects independent of its role in AD, implying that blocking its production may lead to undesirable side effects. Furthermore, γ-secretase is known to act on several different substrates apart from APP (e.g. notch), and so inhibition thereof may also lead to unwanted side effects. There is therefore an interest in methods of treating AD that do not suppress completely the production of Aβ, and do not inhibit the action of γ-secretase.

One such proposed treatment involves modulation of the action of γ-secretase so as to selectively attenuate the production of Aβ(1-42). This results in preferential secretion of the shorter chain isoforms of Aβ, which are believed to have a reduced propensity for self-aggregation and plaque formation, and hence are more easily cleared from the brain, and/or are less neurotoxic. Compounds showing this effect include certain non-steroidal antiinflammatory drugs (NSAIDs) and their analogues (see WO 01/78721 and US 2002/0128319 and Weggen et al *Nature*, 414 (2001) 212-16; Morihara et al, *J. Neurochem.*, 83 (2002), 1009-12; and Takahashi et al, *J. Biol. Chem.*, 278 (2003), 18644-70). Compounds which modulate the activity of PPARα and/or PPARδ are also reported to have the effect of lowering Aβ(1-42) (WO 02/100836). NSAID derivatives capable of releasing nitric oxide have been reported to show improved anti-neuroinflammatory effects and/or to reduce in cerebral Aβ deposition in animal models (WO 02/092072; Jantzen et al, *J. Neuroscience*, 22 (2002), 226-54). US 2002/0015941 teaches that agents which potentiate capacitative calcium entry activity can lower Aβ(1-42).

WO 2005/054193 and WO 2005/013985 disclose further classes of compounds which selectively attenuate Aβ(1-42).

It has now been found that certain tetrahydroindole alkanoic acids and related compounds have the desirable property of selectively inhibiting production of Aβ(1-42).

According to the present invention there is provided a compound of formula I:

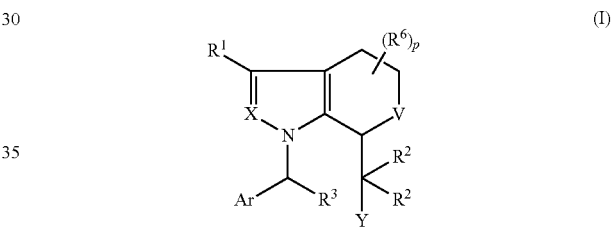

wherein V represents a bond, $CH_2$ or $CH_2CH_2$;

X represents $CR^{1a}$ or N;

Y represents $CO_2H$ or tetrazole;

Ar represents phenyl which optionally bears up to 3 substituents independently selected from hydrocarbon groups of up to 6 carbon atoms and $(CH_2)_m$—Z where m is 0, 1 or 2 and Z represents halogen, $N_3$, CN, $CF_3$, $OCF_3$ or $OR^4$;

$R^1$ represents halogen, CN, $R^4CO$, $CF_3$, $CH_2N(R^4)_2$, a branched $C_{1-10}$alkyl group, a $C_{1-10}$alkenyl group, or a nonaromatic cyclic group of up to 7 ring atoms of which up to 2 may be selected from N, O and S; or when X is $CR^{1a}$, $R^1$ and $R^{1a}$ may complete a fused cycloalkene ring of 5, 6 or 7 members which is optionally substituted with up to 2 $C_{1-4}$alkyl groups;

$R^{1a}$ represents H or $C_{1-4}$alkyl, or combines with $R^1$ as defined above;

with the proviso that when X is CH, $R^1$ is not t-butyl;

each $R^2$ is independently H or $C_{1-4}$alkyl;

$R^3$ is H, hydrocarbon containing up to 10 carbon atoms, benzyloxy$C_{1-4}$alkyl or heterocyclyl$C_{1-4}$alkyl, any of which optionally bears up to 3 substitutents selected from halogen and $CF_3$, or 1 substituent selected from $C_{1-4}$alkoxy and $C_{1-4}$alkylthio, where "heterocyclyl" refers to aromatic or nonaromatic rings of 5 or 6 atoms of which 1, 2 or 3 are selected from N, O and S;

$R^4$ represents H or a hydrocarbon group of up to 7 carbon atoms, optionally substituted with halogen, CN, $CF_3$, OH, $C_{1-4}$alkoxy or $C_{1-4}$alkoxycarbonyl; or two $R^4$ groups attached to a nitrogen atom may complete ring selected from pyrrolidine, piperidine, morpholine, thiomorpholine, tetrahydropyridine and piperazine, any of which rings optionally bearing a substituent selected from $CF_3$, $C_{1-4}$alkyl and phenyl;

$R^5$ represents $R^4$ that is other than H;

p is 0, 1 or 2; and $R^6$ represents $C_{1-6}$alkyl, $C_2$alkenyl or phenyl, benzyl or heteroaryl, said phenyl, benzyl or heteroaryl optionally bearing up to 3 substituents selected from halogen, CN, $CF_3$, $OCF_3$, $OR^4$, $CO_2R^4$, $COR^4$, $OCOR^5$ and $C_{1-4}$alkyl;

or a pharmaceutically acceptable salt or hydrate thereof.

Where a variable occurs more than once in formula I or in a substituent thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits unless otherwise indicated.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-4}$alkoxy" are to be construed in an analogous manner. Most suitably, the number of carbon atoms in such groups is not more than 6.

The term "halogen" as used herein includes fluorine, chlorine, bromine and iodine.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In formula I, V represents a bond, $CH_2$ or $CH_2CH_2$. In a particular embodiment V represents $CH_2$.

In one embodiment, X represents N. In another embodiment, X represents $CR^{1a}$.

$R^3$ represents H or a hydrocarbon group of up to 10 carbon atoms, benzyloxy$C_{1-4}$alkyl or heterocyclyl$C_{1-4}$alkyl, any of which optionally is substituted as defined previously. Examples of hydrocarbon groups represented by $R^3$ include alkyl (especially $C_{1-6}$alkyl such as methyl, ethyl, n-propyl, isopropyl, 2-methylpropyl, n-butyl, 3-methylbutyl and 3,3-dimethylbutyl); substituted alkyl (such as methoxymethyl, methylthiomethyl and 3,3,3-trifluoropropyl); alkenyl (especially $C_{2-6}$alkenyl such as allyl and 3-methylbut-3-enyl), cycloalkyl (especially $C_{3-4}$cycloalkyl such as cyclopropyl, cyclopentyl and cyclohexyl); cycloalkylalkyl (such as cyclopropylmethyl); aryl (such as phenyl and 4-trifluoromethylphenyl) and arylalkyl (such as benzyl, 2-phenylethyl, 2-(3,4-difluorophenyl)ethyl, 2-(3-trifluoromethylphenyl)ethyl). Examples of benzyloxy$C_{1-4}$alkyl groups represented by $R^3$ include 2-(benzyloxyethyl). When $R^3$ represents heterocyclyl$C_{1-4}$alkyl, the heterocyclic group may be 5- or 6-membered and contains up to 3 heteroatoms (typically up to 2 heteroatoms) selected from N, O and S. Said heterocyclic group may be aromatic (such as pyridine, thiophene or furan) or nonaromatic (such as morpholine, thiomorpholine, piperidine or pyrrolidine). Examples of heterocyclyl$C_{1-4}$alkyl groups represented by $R^3$ include 2-morpholin-4-yl)ethyl, 2-(2-pyridyl)ethyl, 2-(3-pyridyl)ethyl and 2-(4-pyridyl) ethyl.

Y represents $CO_2H$ or tetrazole (in particular 1,2,3,4-tetrazol-5-yl), but preferably represents $CO_2H$.

Ar represents phenyl which is optionally substituted as defined previously. Phenyl groups represented by Ar optionally bear up to 3 substituents as defined previously. When said substituents comprise a group represented by $(CH_2)_m-Z$, m is preferably 0 or 1, most typically 0. When Ar represents mono-substituted phenyl, the substituent aptly occupies the 4-position. Examples of suitable substituents include halogen (especially Cl and F), $N_3$, $CF_3$, $OCF_3$, OH, OMe, and $C_{1-4}$alkyl (such as methyl, ethyl, n-propyl and isopropyl). Preferred substituents include Cl, F, $N_3$, $OCF_3$, $CF_3$ and OMe.

Specific examples of groups represented by Ar include phenyl, 4-chlorophenyl, 4-trifluoromethylphenyl, 4-fluorophenyl, 4-azidophenyl, 4-methoxyphenyl, 4-trifluoromethoxyphenyl, 2,4-bis(trifluoromethyl)phenyl, 3,4-dichlorophenyl, 2,4-dichlorophenyl, 2,4,6-trifluorophenyl and 4-iodophenyl, of which 4-trifluoromethylphenyl is particularly preferred.

In one embodiment, $R^1$ is selected from halogen, CN, $R^4CO$, $CF_3$, $CH_2N(R^4)_2$, branched $C_{1-10}$alkyl groups, $C_{1-10}$alkenyl groups, and non-aromatic cyclic groups of up to 7 ring atoms of which up to 2 may be selected from N, O and S. In a subset of this embodiment, $R^1$ is selected from halogen (especially Cl, Br or I), CN, $R^4CO$, $CF_3$, $CH_2N(R^4)_2$, branched $C_{1-10}$alkyl groups (in particular branched $C_{1-6}$alkyl groups), and non-aromatic cyclic groups of up to 7 ring atoms of which up to 2 may be selected from N, O and S.

When X is N, $R^1$ typically does not represent halogen, CN or $R^4CO$.

When $R^1$ represents $R^4CO$, $R^4$ is typically phenyl or $C_{1-4}$alkyl such as methyl or ethyl, and in a particular embodiment $R^1$ is benzoyl. Examples of branched alkyl groups represented by $R^1$ include isopropyl, isobutyl, sec-butyl, tert-butyl and neopentyl. Cyclic groups represented by $R^1$ may be carbocyclic (such as cyclopropyl, cyclobutyl, cyclopentyl, cyclohexyl and cycloheptyl) or heterocyclic (such as tetrahydropyranyl). In a particular embodiment the cyclic group is selected from cyclobutyl, cyclopentyl, cyclohexyl and tetrahydropyran-4-yl.

When $R^1$ represents $CH_2N(R^4)_2$, the $R^4$ groups very suitably complete a ring as defined previously. Examples of rings represented by $N(R^4)_2$ include pyrrolidinyl, piperidinyl, morpholinyl, thiomorpholinyl, 4-methylpiperazinyl, 4-phenylpiperazinyl and 4-trifluoromethyl-1,2,3,6-tetrahydropyridinyl. In a particular embodiment, $R^1$ represents morpholin-4-ylmethyl. Alternatively, one $R^4$ group very suitably represents H or $C_{1-4}$alkyl and the other represents a hydrocarbon group of up to 7 carbon atoms, such as $C_{1-6}$alkyl, $C_{3-6}$cycloalkyl, phenyl or benzyl, optionally substituted as defined previously. Examples of groups represented by $CH_2N(R^4)_2$ thus include anilinomethyl, benzylaminomethyl and cyclohexylaminomethyl.

In another embodiment, X is $CR^{1a}$ and $R^1$ and $R^{1a}$ complete a fused cycloalkene ring of 5, 6 or 7 members which is optionally substituted with up to 2 $C_{1-4}$alkyl groups. For example, $R^1$ and $R^{1a}$ may complete a fused cyclohexene ring, and the compound of formula I is thus an octahydrocarbazole derivative. In a particular embodiment, the fused cycloalkene ring is unsubstituted. In another particular embodiment, the fused cycloalkene ring is substituted with up to two $C_{1-4}$alkyl groups, e.g. methyl groups.

When present, $R^{1a}$ represents H or $C_{1-4}$alkyl, or combines with $R^1$ as described above. Suitable alkyl groups include methyl, ethyl and isopropyl, in particular methyl. In one embodiment, $R^{1a}$ represents $C_{1-4}$alkyl and $R^1$ represents halogen, CN or $R^4CO$. In a further embodiment, $R^{1a}$ represents H and $R^1$ represents $CF_3$, a branched alkyl group or a carbocyclic or heterocyclic group as described above, with the proviso that $R^1$ is not tert-butyl.

Each $R^2$ is independently H or $C_{1-4}$alkyl such as methyl or ethyl. Preferably one $R^2$ is H and the other is H or methyl. Most preferably, both $R^2$ groups are H.

When present, $R^6$ represents linear or branched $C_{1-4}$alkyl (preferably $C_{1-4}$alkyl) such as methyl, ethyl, n-propyl, isopropyl or t-butyl, $C_{2-6}$ alkenyl such as vinyl or allyl, or phenyl, heteroaryl or benzyl which is optionally substituted as defined previously. Preferred substituents include halogen (especially Cl or F), $OCH_3$, $OCF_3$, $CF_3$ and $C_{1-4}$alkyl (such as methyl). A preferred heteroaryl group is pyridyl, especially 3-pyridyl. Examples of groups represented by $R^6$ include methyl, ethyl, isopropyl, vinyl, 3-pyridyl, phenyl, 4-chlorophenyl, 3-fluorophenyl, 4-fluorophenyl, 4-fluoro-3-methylphenyl, 4-methoxyphenyl, 3,4-dichlorophenyl, 3,4-difluorophenyl and 2,5-dimethylphenyl. Preferred examples include 4-fluorophenyl. An $R^6$ group may be attached at any available position of the ring, including the carbon atom bearing the —$C(R^2)_2$—Y moiety and any carbon atom included in V. Where two $R^6$ groups are present, they may be the same or different and may be attached to the same or different ring positions. When p is 2, preferably not more than one of the $R^6$ groups is optionally-substituted phenyl, heteroaryl or benzyl. In a particular embodiment, p is zero.

A subset of the compounds of Formula I is defined by Formula II:

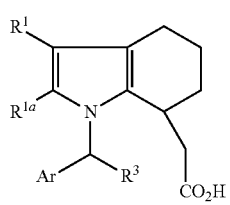

II wherein Ar, $R^1$, $R^{1a}$, and $R^3$ have the same definitions and preferred identities as before.

A subset of the compounds in accordance with formula II consists of the compounds in which $R^1$ is Cl, Br, I, CN, $CH_3CO$, PhCO or $CH_2N(R^4)_2$ and $R^{1a}$ is $C_{1-4}$alkyl.

Another subset of the compounds of formula II consists of those in which $R^{1a}$ is H and $R^1$ is $CF_3$, a branched $C_{1-4}$alkyl group, or a $C_{3-7}$cycloalkyl group, or is tetrahydropyran-4-yl, with the proviso that $R^1$ is not tert-butyl.

In both of these subsets of formula II, Ar is very suitably 4-trifluoromethylphenyl.

A second subset of the compounds of formula I is defined by formula III:

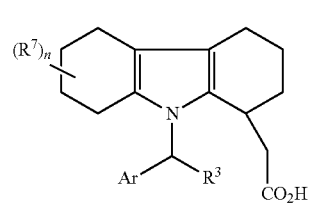

III wherein n is 0, 1 or 2, $R^7$ is $C_{1-4}$alkyl (eg. methyl), and Ar and $R^3$ have the same definitions and preferred identities as before. In formula III, Ar preferably represents 4-trifluoromethylphenyl.

A third subset of the compounds of formula I is defined by formula IV:

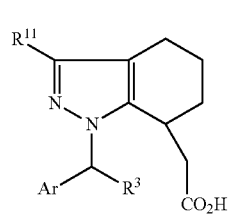

IV where $R^{11}$ represents $CF_3$, branched $C_{1-6}$alkyl, $C_{3-7}$cycloalkyl or tetrahydropyran-4-yl, and Ar, and $R^3$ have the same definitions and preferred identities as before.

In formula IV, Ar is very suitably 4-trifluoromethylphenyl.

In one subset of formula IV, $R^{11}$ is t-butyl. In another subset, $R^{11}$ is branched $C_{1-6}$alkyl that is other than t-butyl. In a third subset, $R^{11}$ is $C_{3-7}$cycloalkyl.

Compounds of formula II in which $R^1$ represents Cl, Br or I and $R^{1a}$ is $C_{1-4}$alkyl have a particular utility as starting materials for the synthesis of further compounds having the property of selectively inhibiting the production of $A\beta(1\text{-}42)$, e.g. compounds of a type disclosed in WO2005/108362. Therefore, according to a further aspect of the invention, there is provided a process for preparing a compound of formula V:

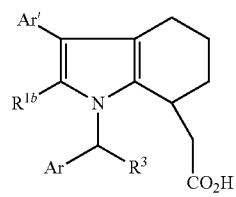

V comprising reaction of compound of formula VI:

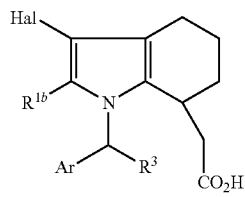

with a boronic acid derivative Ar'—B(OR)$_2$;
wherein:
Ar' represents a phenyl, naphthyl or heteroaryl ring system of up to 10 ring atoms up to 3 of which are selected from N, O and S, any of which ring systems optionally bearing up to 3 substituents selected from halogen, NO$_2$, CF$_3$, OCF$_3$, CN, C$_{1-4}$alkyl, C$_{1-4}$alkoxy or C$_{1-4}$alkoxycarbonyl;

Hal represents Cl, Br or I;
each R represents H or C$_{1-4}$alkyl or the two R groups together complete a cyclic boronate ester;
R$^{1b}$ represents C$_{1-4}$alkyl; and
Ar and R$^3$ have the same definitions and preferred identities as before.

The reaction is an example of the Suzuki reaction and may be carried out in the presence of a Pd(II) catalyst such as bis(diphenylphosphino)ferrocene dichloropalladium(II) (Pd (dppf)Cl$_2$) in the presence of base (such as sodium carbonate) in an aqueous organic mixture such as aqueous dioxan at elevated temperature (e.g. 100° C., or about 170° C. with microwave heating). Very suitably, the carboxylic acid in formula VI is protected (e.g as a methyl or ethyl ester) prior to the reaction, and regenerated subsequently (e.g. by alkaline hydrolysis).

Hal preferably represents Br or I.

Heteroaryl groups represented by Ar' may be monocyclic or bicyclic, such as pyrrole, furan, thiophene, oxazole, isoxazole, thiazole, isothiazole, pyrazole, imidazole, triazole, oxadiazole, thiadiazole, pyridine, pyrimidine, pyrazine, pyridazine, indole, benzofuran, benzothiazole, quinoline and isoquinoline.

When Ar' bears one or more substituents, said substituent(s) are typically selected from halogen (especially Cl or F), CF$_3$, OCF$_3$, CN and C$_{1-4}$alkyl (especially methyl). Certain compounds in accordance with formula V, obtainable by the above process, are themselves novel and form a further aspect of the invention. Specifically, in this aspect the invention provides a compound of formula V or a pharmaceutically acceptable salt thereof wherein:

Ar represents 4-trifluoromethylphenyl, R$^3$ represents 3-methylbutyl, R$^{1b}$ represents isopropyl and Ar' represents 4-pyridyl;

or wherein Ar represents 4-trifluoromethylphenyl, R$^3$ represents 3-methylbutyl, R$^{1b}$ represents methyl and Ar' represents 4-(trifluoromethyl)phenyl, 2,4-difluorophenyl, 4-chlorophenyl, 4-(trifluoromethoxy)phenyl, 2,4-dichlorophenyl, 2-(trifluoromethyl)phenyl, 3,4-dichlorophenyl, 2,3-dichlorophenyl, 2,5-difluorophenyl, 2,5-dichlorophenyl, 5-indolyl, 6quinolyl, 7-thiophenyl, 5-pyrimidinyl or 4-pyrazolyl.

These and other compounds in accordance with formula V may be used in the same manner and for the same therapeutic purposes as the compounds of formula I as described herein.

Specific examples of compounds in accordance with formula I are provided in the Examples appended hereto.

Compounds of formula I in which X represents CH and R$^1$ represents CF$_3$, alkyl, alkenyl, cycloalkyl or heterocyclyl may be obtained by reaction of an imine (1) with a nitro-olefin (2):

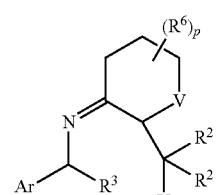

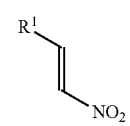

wherein V, Ar, Y, p, R$^2$, R$^3$, R$^6$ and R$^1$ have the same meanings as before. The reaction takes place in toluene solution, eg at reflux or by heating in a microwave apparatus.

Imines of formula (I) are conveniently generated in situ by reaction of an amine (3) with a cyclohexanone of formula (4):

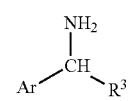

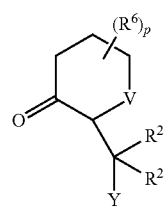

where V, Ar, R$^3$, Y, p, R$^2$ and R$^6$ have the same meanings as before. The reaction can be carried out in toluene with azeotropic removal of water.

Amines (3) may be obtained by treating ketones Ar—CO—R$^3$ with hydroxylamine and hydrogenating the resulting oximes over Raney nickel. Alternatively, ketones Ar—CO—R$^3$ may be condensed with α-methylbenzylamine and the resulting imines reduced (using NaBH$_4$) to provide bis(benzylamines) ArCH(R$^3$—NH—CH(CH$_3$)Ph, from which the desired amines (3) are obtained by hydrogenation over Pd/C. Use of a chiral α-methylbenzylamine facilitates isolation of amines (3) as single enantiomers, enabling control of the stereochemistry at one of the chiral centres in formula I.

Compounds of formula I in which X represents CR$^{1a}$ and R$^1$ is CF$_3$, alkyl, alkenyl, cycloalkyl or heterocyclyl may be obtained by reaction of an amine (3) with a 1,4-dicarbonyl compound (5):

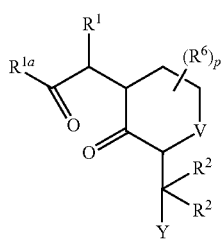

(5)

The reaction takes place in toluene solution in the presence of an acid catalyst (eg. acetic acid) with azeotropic removal of water. Alternatively, the reaction can be carried out in dichloromethane at −78° C. in the presence of triethylamine and TiCl$_4$.

Compounds (5) are available by reaction of an enamine (6):

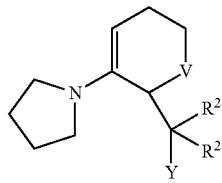

(6)

with a halo-ketone $R^{1a}$—CO—CH($R^1$)-Hal where Hal is chloride or bromide. The reaction takes place in DMF at ambient temperature and is particularly suitable when $R^1$ is H or alkyl.

Enamines (6) are formed from ketones (4) by refluxing with pyrrolidine in toluene solution using an acid catalyst such as acetic acid with azeotropic removal of water.

A preferred route to dicarbonyl compounds (5) comprises oxidative cleavage of olefins (7):

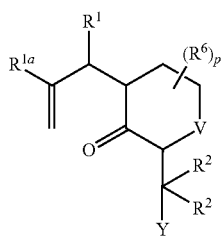

(7)

where V, Y, p, $R^1$, $R^{1a}$, $R^2$ and $R^6$ have the same meanings as before. The cleavage may be effected by ozonolysis in methanol/dichloromethane, or alternatively by treatment with RuCl$_3$ and NaIO$_4$. Ozonolysis is preferred when $R^{1a}$ is H.

Olefins (7) may be obtained by treatment of ketones (4) with triethylorthoformate, and reaction of the resulting diethyl ketals with an allylic alcohol (8):

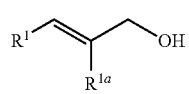

(8)

where $R^1$ and $R^{1a}$ have the same meanings as before. The reaction may be carried out at about 125° C. in the presence of propionic acid. The initial product is an enol ether which undergoes Claisen rearrangement to provide the olefin (7).

Compounds of formula I in which X is N may be obtained by reaction of diketones (9) with hydrazines (10):

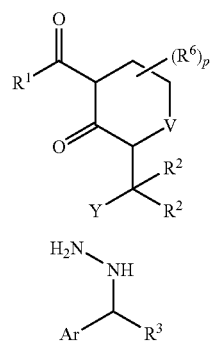

(9)

(10)

The reaction takes place in refluxing ethanol. Diketones (9) are available by reaction of enamines (6) with $R^1$—COCl. Hydrazines (10) are available by reaction of Ar—CH($R^3$)—Br with hydrazine hydrate in isopropanol at 70° C. (see also EP 0234708).

A preferred route to compounds of formula IV comprises N-alkylation of tetrahydroindazoles (11) with Ar—CH($R^3$)-Hal, followed by oxidation of the allyl group to the corresponding carboxylic acid.

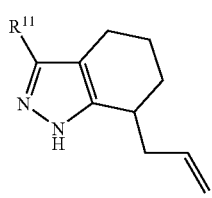

(11)

(12)

where Hal is Cl, Br or I and $R^{11}$, $R^3$ and Ar have the same meanings as before. The alkylation takes place at ambient temperature in DMF in the presence of sodium hydride. The oxidation may be carried out using excess sodium periodate in the presence of RuCl$_3$ hydrate as catalyst in a CCl$_4$/MeCN/H$_2$O mixture. Compounds (11) are obtainable by treating diketones (12) with hydrazine (e.g. in ethanol at ambient temperature). Diketones (12) are obtainable by reaction of 2-allylcyclohexanone with $R^{11}$CO—Bt where Bt refers to benzotriazol-1-yl. The reaction takes place at −70° C. to ambient temperature in THF in the presence of strong base such as lithium hexamethyldisilazide.

Compounds of formula I in which $R^1$ is halogen, CN or $R^4$CO may be obtained by reaction of the corresponding compounds in which $R^1$ is H with, respectively, an N-halosuccinimide, chlorosulfonyl isocyanate or $R^4$COCl. The reaction with N-bromo- or N-chlorosuccinimide may be carried out at −78° C. in THF, and the reaction with N-iodosuccinimide at −20° C. in THF. The reaction with chlorosulfonyl isocyanate may be carried out at −78° C. in DMF/acetonitrile mixture, and the reaction with $R^4COCl$ may be carried out in dichloromethane in the presence of $AlCl_3$ at ambient temperature. The compounds of formula I in which $R^1$ is H are obtainable by analogous routes to those described above in which $R^1$ is alkyl, alkenyl, cycloalkyl or heterocyclyl.

Compounds of formula I in which $R^1$ is $CH_2N(R^4)_2$ may be obtained by treatment of the corresponding compounds in which $R^1$ is H with $POCl_3$ and DMF in toluene at about 70° C., and reaction of the resulting aldehydes with $(R^4)_2NH_2$ and sodium triacetoxyborohydride, e.g. in chloroform at room temperature.

During all of the chemical processes described above, a carboxylic acid group represented by Y is preferably protected as the methyl ester or ethyl ester, the free acid being regenerated by hydrolysis in a final step, e.g. using LiOH in aqueous THF or dioxan.

Where they are not commercially available, the starting materials used in the schemes outlined above may be obtained by published routes or simple adaptations thereof. Suitable methods are described in the Examples section herein.

Since the compounds of Formula I have at least one asymmetric centre, they accordingly exist in enantiomeric forms. If desired, the individual enantiomers may be isolated in pure form by conventional means. For example, a racemic mixture may be resolved into its component enantiomers by preparative chiral HPLC, or by treatment with an optically pure amine to form diastereomeric salt pairs, separable by fractional crystallisation, from which the optically pure acids may be regenerated. Similarly, a racemic acid may be reacted with an optically pure alcohol or amine to form pairs of diastereomeric esters or amides which may be separated by chromatography or fractional crystallisation and hydrolysed to yield enantiomerically-pure acids. These resolution techniques may equally well be practised on the synthetic precursors of the compounds of Formula I, and the resulting optically-pure intermediates used to prepare compounds of Formula I in optically-pure form.

The invention further provides a pharmaceutical composition comprising compound of formula I or pharmaceutically acceptable salt thereof and a pharmaceutically acceptable carrier.

Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The invention also provides a compound of formula I or a pharmaceutically acceptable salt thereof for use in therapy, in particular for use in treatment or prevention of a disease associated with deposition of Aβ in the brain.

The invention further provides the use of a compound of formula I or a pharmaceutically acceptable salt thereof for the manufacture of a medicament for treatment or prevention of a disease associated with deposition of Aβ in the brain.

The disease associated with deposition of Aβ in the brain is typically Alzheimer's disease (AD), cerebral amyloid angiopathy, multi-infarct dementia, dementia pugilistica or Down syndrome, preferably AD.

In another aspect, the invention provides the use of a compound of Formula I as defined above, or a pharmaceutically acceptable salt thereof, in the manufacture of a medicament for treating, preventing or delaying the onset of dementia associated with Alzheimer's disease, cerebral amyloid angiopathy, HCHWA-D, multi-infarct dementia, dementia pugilistica or Down syndrome.

The invention also provides a method of treating or preventing a disease associated with deposition of Aβ in the brain comprising administering to a patient in need thereof a therapeutically effective amount of a compound of Formula I as defined above or a pharmaceutically acceptable salt thereof.

In a further aspect, the invention provides a method of treating, preventing or delaying the onset of dementia associated with Alzheimer's disease, cerebral amyloid angiopathy, HCHWA-D, multi-infarct dementia, dementia pugilistica or Down syndrome comprising administering to a patient in need thereof a therapeutically effective amount of a compound of Formula I as defined above or a pharmaceutically acceptable salt thereof.

The compounds of Formula I modulate the action of γ-secretase so as to selectively attenuate production of the (1-42) isoform of Aβ without significantly lowering production of the shorter chain isoforms such as Aβ(1-40). This results in secretion of Aβ which has less tendency to self-aggregate and form insoluble deposits, is more easily cleared from the brain, and/or is less neurotoxic. Therefore, a further aspect of the invention provides a method for retarding, arresting or preventing the accumulation of Aβ in the brain comprising administering to a subject in need thereof a therapeutically effective amount of a compound of Formula I as defined above or a pharmaceutically acceptable salt thereof.

Because the compounds of formula I modulate the activity of γ-secretase, as opposed to suppressing said activity, it is believed that the therapeutic benefits described above will be obtained with a reduced risk of side effects, e.g. those that might arise from a disruption of other signalling pathways (e.g. Notch) which are also controlled by γ-secretase.

In one embodiment of the invention, the compound of Formula I is administered to a patient suffering from AD, cerebral amyloid angiopathy, HCHWA-D, multi-infarct dementia, dementia pugilistica or Down syndrome, preferably AD.

In an alternative embodiment of the invention, the compound of Formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a threefold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of Formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of Formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42).

A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry*, 141 (1984), 1356-64).

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which inhibit the secretion of Aβ (including γ-secretase inhibitors, β-secretase inhibitors, and GSK-3α inhibitors), compounds which inhibit the aggregation of Aβ, and antibodies which selectively bind to Aβ. Such additional compounds further include growth hormone secretagogues, e.g. as described in WO 2004/110443 and WO 2004/080459.

In this embodiment of the invention, the amyloid modifier may be a compound which inhibits the secretion of Aβ, for example an inhibitor of γ-secretase (such as those disclosed in WO 01/53255, WO 01/66564, WO 01/70677, WO 01/90084, WO 01/77144, WO 02/30912, WO 02/36555, WO 02/081435, WO 02/081433, WO 03/018543, WO 03/013506, WO 03/013527, WO 03/014075, WO 03/093251, WO 03/093252, WO 03/093253, WO 03/093264, WO 2004/

031137, WO 2004/031138, WO 2004/031139, WO 2004/039370, WO 2004/039800, WO 2004/101538, WO 2004/101539 and WO 2005/030731), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621.

Alternatively, the amyloid modifier may be a compound which inhibits the aggregation of Aβ or otherwise attenuates is neurotoxicicity. Suitable examples include chelating agents such as clioquinol (Gouras and Beal, *Neuron*, 30 (2001), 641-2) and the compounds disclosed in WO 99/16741, in particular that known as DP-109 (Kalendarev et al, *J. Pharm. Biomed. Anal.*, 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466. Suitable antibodies also include those specific to Aβ-derived diffusible ligands (ADDLS), as disclosed in WO 2004/031400.

As used herein, the expression "in combination with" requires that therapeutically effective amounts of both the compound of Formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of Formula I.

The ability of the compounds of Formula I to selectively inhibit production of Aβ(1-42) was determined using the following assay:

Cell-Based γ-Secretase Assay

Human SH-SY5Y neuroblastoma cells overexpressing the direct γ-secretase substrate SPA4CT were induced with sodium butyrate (10 mM) for 4 hours prior to plating. Cells were plated at 35,000 cells/well/100 μl in 96-well plates in phenol red-free MEM/10% FBS, 50 mM HEPES, 1% Glutamine and incubated for 2 hrs at 37° C., 5% $CO_2$.

Compounds for testing were diluted into $Me_2SO$ to give a ten point dose-response curve. Typically 10 μl of these diluted compounds in $Me_2SO$ were further diluted into 182 μl dilution buffer (phenol red-free MEM/10% FBS, 50 mM HEPES, 1% Glutamine) and 10 μl of each dilution was added to the cells in 96-well plates (yielding a final $Me_2SO$ concentration of 0.5%). Appropriate vehicle and inhibitor controls were used to determine the window of the assay.

After incubation overnight at 37° C., 5% $CO_2$, 10 μl and 50 μl media were transferred into a fresh Costar round-bottom 96-well plate for detection of Aβ(40) and Aβ(42) peptides, respectively. 40 μl Origen buffer (PBS, 2% BSA, 0.2% Tween-20) was added to the Aβ(40) wells followed by the addition of 25 μl the respective antibody premixes to the wells:

Aβ(40) premix: 1 μg/ml ruthenylated G2-10 antibody, 4 μg/ml biotinylated 4G8 antibody diluted in Origen buffer Aβ(42) premix: 0.5 μg/ml ruthenylated G2-11 antibody, 4 μg/ml biotinylated 4G8 antibody diluted in Origen buffer (Biotinylated 4G8 antibody supplied by Signet Pathology Ltd; G2-10 and G2-11 antibodies supplied by Chemicon)

After overnight incubation of the assay plates on a shaker at 4° C., the Origen M8 Analyser (Igen Inc.) was calibrated according to the manufacturer's instructions. 25 μl of streptavidin magnetic bead (Dynal) premix (400 μg/ml streptavidin beads/ml in Origen buffer) was added to the assay plates and incubated on a shaker for 15 minutes. 150 μl Origen buffer was added to each well and the plates were read on the Origen M8 Analyser according to the manufacturer's instructions.

Cell viability was measured in the corresponding cells after removal of the media for the Aβ assays by a colorimetric cell proliferation assay (CellTiter 96™ AQ assay, Promega) utilizing the bioreduction of MTS (Owen's reagent) to formazan according to the manufacturer's instructions. Briefly, 5 μl of 10×MTS/PES was added to the remaining 50 μl of media before returning to the incubator. The optical density was read at 495 nm after ~4 hours.

LD50 and $IC_{50}$ values for inhibition of Aβ(40) and Aβ(42) were calculated by nonlinear regression fit analysis using the appropriate software (eg. Excel fit). The total signal and the background were defined by the corresponding $Me_2SO$ and inhibitor controls.

The compounds of the invention give $IC_{50}$ values for Aβ(1-42) inhibition that are at least 2-fold lower than the corresponding IC$_{50}$ values for Aβ(1-40) inhibition, typically at least 5-fold lower, and in the preferred cases at least 50-fold lower.

EXAMPLES

Intermediate 1

(1S)-4-Methyl-1-[4-(trifluoromethyl)phenyl]pentyl amine

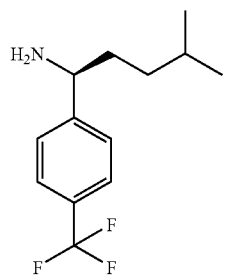

Step 1

Magnesium (17 g) was stirred 10 min under nitrogen then THF (400 mL) was added. 1-Bromo-4-methylbutane (5 mL) was added and the mixture stirred 5 min until the reaction initiated (exotherm) the reminder of the bromomethylbutane (100 g, 0.672 mol) was added keeping the temp below 35° C. (water bath). The mixture was stirred 1 hr at RT and a solution of 4-trifluoromethylbenzonitrile (100 g, 0.584 mol) in toluene (1 L) containing some CuBr was added dropwise keeping the temp 25° C. The solution was stirred 1 h and quenched carefully with 15% H$_2$SO$_4$ (exotherm). The organic layer was decanted, washed with brine, dried over (MgSO$_4$) and concentrated in vacuo. The oil was purified by column chromatography on silica using isohexane as eluant to give 4-methyl-1-[4-(trifluoromethyl)phenyl]pentan-1-one (126 g) which solidified on standing. $^1$H NMR δ (ppm)(CDCl$_3$): 8.06 (2H, d, J 8.1 Hz), 7.73 (2H, d, J 8.1 Hz), 2.99 (2H, app. t, J 7.4 Hz), 1.68-1.60 (3H, m), 0.96 (6H, d, J 6.3 Hz).

Step, 2

To a solution of 4-methyl-1-[4-(trifluoromethyl)phenyl]pentan-1-one [Step 1] (70 g, 0.312 mol) in toluene (500 mL) at RT was added S-phenylethylamine (44.5 g, 0.374 mol) and zinc chloride (2 g, 15.61 mmol). A Dean-Stark apparatus was attached and the reaction refluxed for 16 h. The reaction was cooled, washed with 1N NaOH (800 mL), saturated ammonium chloride (x3), dried (MgSO$_4$) and evaporated to give 4-methyl-1-[4-(trifluoromethyl)phenyl]pentylidene) [(1S)-1-phenylethyl]amine (87 g) as a 3:1 mixture of isomers as an oil that was taken directly into Step 3.

Step 3

To a solution of {4-methyl-1-[4-(trifluoromethyl)phenyl]pentylidene}[(1S)-1-phenylethyl]amine [Step 2] (87 g, 0.25 mol) in methanol (0.5 L) at −20° C. was added sodium borohydride (10 g, 0.263 mol) portionwise. The solution was stirred 1/2 hrs at 0° C. and quenched carefully with 1N HCl, basified with 4N NaOH and extracted with EtOAc. The organic layer was decanted, dried (MgSO$_4$) and evaporated to give 85 g of {4-methyl-1-[4-trifluoromethyl)phenyl]pentyl}[(1S)-1-phenylethyl]amine as a 3:1 mixture of diastereomers by NMR. This was dissolved in methanol (250 mL) and phthalic acid (40 g) was added. The solution was stirred at RT when it started to crystallise. The mixture was stirred 2 h at RT and the solid was then filtered to give single diastereomer {(1S)-4-methyl-1-[4-(trifluoromethyl)phenyl]pentyl}[(1S)-1-phenylethyl]amine as the phthalic acid salt (70.5 g). A small portion of the phthalic acid salt was partitioned between CDCl$_3$ and aqueous K$_2$CO$_3$ to form the free base and a $^1$H NMR was taken; $^1$H NMR δ (ppm) (CDCl$_3$): 7.57 (2H, d, J 8.0 Hz), 7.33 (5H, dd, J 7.6, 9.8 Hz), 7.16 (2H, d, J 6.9 Hz), 3.40 (1H, q, J 6.7 Hz), 3.32 (1H, t, J 6.9 Hz), 1.66-1.48 (2H, m), 1.46-1.32 (1H, m), 1.26 (3H, d, J 6.7 Hz), 1.19-1.09 (1H, m), 0.95-0.85 (1H, m), 0.79 (3H, d, J 3.6 Hz), 0.77 (3H, d, J 3.5 Hz).

Step 4

A suspension of {(1S)-4-methyl-1-[4-trifluoromethyl)phenyl]pentyl}[(1S)-1-phenylethyl]amine phthalate salt [Step 3] (70 g, 0.135 mol) and 110% palladium on carbon (900 mg) in EtOH (300 mL) was hydrogenated under 40 psi at 57° C. for 3.5 h. The catalyst was removed by filtration and the filtrate concentrated to a half, diluted with ethyl acetate, washed three times with 4N NaOH then with brine, dried (MgSO$_4$) and evaporated to give the title compound as a liquid (60 g); $^1$H NMR δ (ppm) (CDCl$_3$): 7.58 (2H, d, J 8.2 Hz), 7.43 (2H, d, J 8.0 Hz), 3.93 (1H, t, J 6.8 Hz), 1.69-1.59 (2H, m), 1.57-1.49 (1H, m), 1.28-1.18 (1H, m), 1.11-1.01 (1H, m), 0.87 (3 H, d, J 1.8 Hz), 0.85 (3 H, d, J 1.8 Hz); m/z (ES$^+$) 246 (M+H$^+$); $α_D^{20}$=−9.0 (c=1, CHCl$_3$).

Intermediate 2

(1R)-4-Methyl-1-[4-(trifluoromethyl)phenyl]pentyl amine

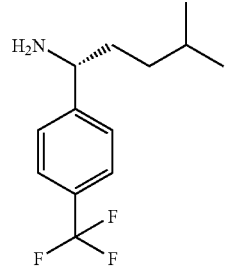

The enantiomer (+){(1R)-4-methyl-1-[4-trifluoromethyl)phenyl]pentyl amine was prepared as Intermediate 1 employing R-phenylethylamine instead of S-phenylethyl amine in Step 2.

Intermediate 3

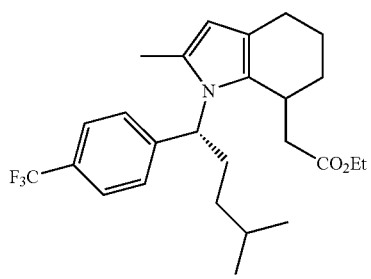

Step 1

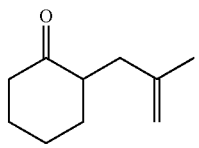

2-Methylprop-2-en-1-ol (57 g, 0.79 mol) and 1,1-diethoxycyclohexane (190 g, 1.1 mol) and propionic acid (10 mL) were heated to 170° C. for 16 h under reflux. The mixture was cooled, a Dean-Stark trap was fitted, and the mixture reheated to 170° C. The volatile material (mainly ethanol) was removed using the trap, and heating was continued for a further 30 h, prior to cooling to room temperature. The resulting oil was purified by distillation (bp 76-80° C./50 mbar). Colourless oil (104.5 g, 87%). $^1$H NMR δ (ppm) (CDCl$_3$): 4.76 (1H, s), 4.66 (1H, s), 2.25-2.50 (5H, m), 2.0-2.15 (2H, m), 1.4-1.8 (5H, m), 1.25-1.35 (2H, m).

Step 2

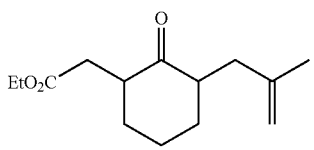

Prepared by alkylation of the product of Step 1 with ethyl bromoacetate in THF at −78° C. in the presence of KHMDS using the procedure described in Example 12 Step 2.

Step 3

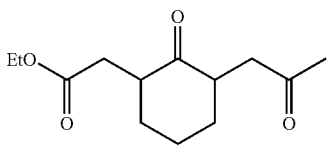

To a vigorously stirred suspension of ethyl [3-(2-methylprop-2-en-1-yl)-2-oxocyclohexyl]acetate [Step 2] (25 g, 105 mmol) and sodium periodate (89.8 g, 420 mmol) in CCl$_4$ (50 mL)/MeCN (50 mL) and water (75 mL) was added ruthenium trichloride monohydrate (0.44 g, 2.1 mmol), and stirring was continued for 16 h. The resulting mixture was partitioned between water (850 mL) and DCM (850 mL), and the aqueous layer/solid residue was extracted with DCM (×2). The combined organic phases were washed (brine), dried (sodium sulphate) and concentrated to give a dark-brown oil, which was purified by flash chromatography (Biotage SP1, 65M, 10-40% EtOAc/isohexane) gave the mixture of diastereoisomers as a pale yellow oil (11 g, 43%) $^1$H NMR δ (ppm) (CDCl$_3$): 4.09-4.15 (2 H, m), 2.65-3.05 (4H, m), 2.35-2.45 (1H, m), 2.05-2.2 (4H, m), 1.6-2.0 (5H, m) 1.3-1.45 (1H, m), 1.25-1.3 (3H, m).

Step 4

The product of Step 3 (2.0 g, 8.33 mmol), Intermediate 2 (2.04 g, 8.33 mmol) and 4-methylbenzenesulfonic acid hydrate (0.16 g, 0.83 mmol) were dissolved in toluene (7 mL) and heated to 150° C. for 48 h with a Dean-Stark trap. The mixture was cooled, and partitioned between DCM and NaHCO$_3$(aq). The organic phase was dried (sodium sulfate), and concentrated under reduced pressure to give a dark brown oil, which was purified by flash chromatography (Biotage SP1, 40M, 0->15% EtOAc/isohexane) to give a pale yellow oil. Mixture of diastereoisomers $^1$H NMR (360 MHz), δ (ppm) (CDCl$_3$): 7.54 (2H, t), 7.14 (1H, d), 7.03 (1H, d), 5.71 (1H, d), 5.23-5.17 (1H, m), 4.14-3.99 (2H, m), 3.28-2.94 (1H, m) 2.50-0.83 (25H, m).

Intermediate 4

Mixture of ethyl (2-ethoxycyclohex-2-en-1-yl)acetate and ethyl (2,2-diethoxycyclohexyl)acetate

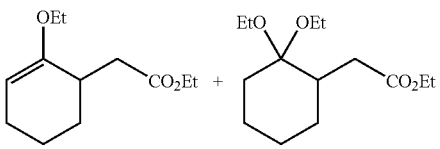

To a stirred solution of ethyl (2-oxocyclohexyl)acetate (40.2 mL, 0.228 mol) in ethanol (66 mL) was added p-toluenesulfonic acid (422 mg, 2.28 mmol) and triethyl orthoformate (113 mL, 0.684 mol). The reaction mixture was heated to 95° C. and stirred for 16 h. The mixture was concentrated in vacuo at 60° C. for 2½ hours to remove excess triethyl orthoformate. The mixture was used crude in subsequent reactions. $^1$H NMR δ (ppm) (CDCl$_3$): 4.60 (1H, t, J 3.9 Hz), 4.17-4.09 (4H, m), 3.76-3.58 (4H, m), 3.47-3.41 (3H, m), 3.11 (1H, s), 2.71-2.63 (2H, m), 2.58-2.40 (1H, m), 2.37-2.09 (4H, m), 2.07-1.97 (4H, m), 1.91-1.33 (8H, m), 1.31-1.16 (14H, m).

Intermediate 5

1-Bromo-4-methyl-1-(4-(trifluoromethyl)phenyl) pentane

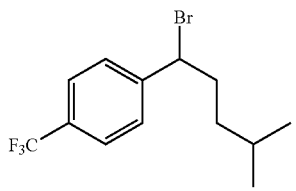

Sodium borohydride (2.8 g, 0.074 mol) was added portionwise to a solution of 4-methyl-1-[4-(trifluoromethyl)phenyl]pentan-1-one [Intermediate 1; Step 1] in EtOH (50 mL) cooled in ice. When addition was complete (30 min) the mixture was stirred at RT for 1 h then quenched with NH$_4$Cl solution (50 mL) followed by 2N HCl (20 mL). Extraction with ether (3×50 mL) followed by drying (MgSO$_4$) and concentration of the organic phase gave 4-methyl-1-(4-(trifluoromethyl)phenyl)pentan-1-ol as a colourless oil.

PBr$_3$ (5 g, 0.018 mol) was added dropwise to a solution of this alcohol (5 g, 0.02 mol) stirring at RT. The mixture was stirred at RT for 1 h and then poured into ice and the mixture extracted with Et$_2$O (3×20 mL). The organic phase was dried (MgSO$_4$) and concentrated to give the bromide as an oil. $^1$H NMR δ (ppm) (CDCl₃): 7.6 (2H, d, J 8 Hz), 7.49 (2H, d, J 8 Hz), 4.90 (1H, t, J 7 hz), 2.4-1.1 (5H, m), 0.89 (6H, d, J 7 Hz).

Intermediate 6

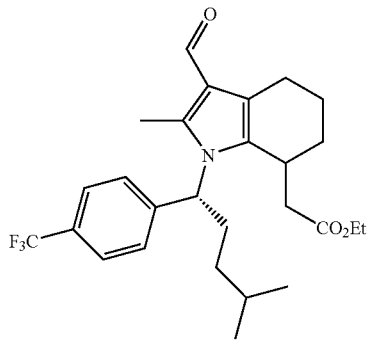

To a stirred solution of DMF (2.32 ml, 30.03 mmol) in dry toluene (10 ml) was added POCl₃ (4.14 g, 27.03 mmol) dropwise. The resulting biphasic mixture was stirred at 70° C. for 5 min, prior to addition of Intermediate 2 as a solution in toluene (10 ml). The resulting solution was stirred at this temperature for 2 h, and then poured onto saturated sodium acetate (aq). The aqueous phase was extracted with EtOAc, the combined organic phases were washed (brine), dried (sodium sulfate) and concentrated. Purification by flash chromatography (Biotage SP1, 25S, 2-30% EtOAc/isohexane) gave a colourless oil as a 1:1 mixture of diastereoisomers. 1H NMR (360 MHz, CDCl₃): δ 9.91 (m, 1 H), 7.60 (t, 2 H), 7.16 (t, 2 H), 5.30 (m, 1 H), 4.13-3.99 (m, 2 H), 3.21 (d, 1 H), 2.95 (t, 1 H), 2.70-1.18 (m, 14 H), 0.98-0.90 (m, 8 H).

Intermediate 7

(1S)-3-Phenyl-1-[4-(trifluoromethyl)phenyl]propyl amine hydrochloride salt

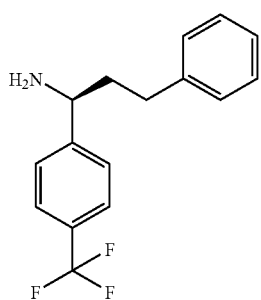

2-methyl-N-{(1S)-3-phenyl-1-[4-(trifluoromethyl)phenyl]propyl}propane-2-sulfinamide (*JACS*, 2005, 127, 1092-3) (8.3 g, 21.7 mmol) was dissolved in methanol (50 mL) and a 4M solution of HCl in dioxane (10.8 mL) was added. The solution was stirred at RT for 1 h then concentrated. The residue was triturated with isohexane to give a colourless solid which was collected by filtration. ¹H NMR (400 MHz), δ (ppm) (DMSO-D⁶): 8.7 (3H, s), 7.85 (2H, d, J 8.3 Hz), 7.77 ((2H, d, J 8.3 Hz), 7.29-7.26 (2H, m), 7.20-7.13 (3H, m), 4.36 (1H, m), 2.4-2.35 (2H, m), 2.35-2.25 (m, 1H), 2.2-2.1 (1H, m).

Example 1

(3-Bromo-2-methyl-1-{(1R)-4-methyl-1-[4-trifluoromethyl)phenyl]pentyl}-4,5,6,7-tetrahydro-1H-indol-7-yl)acetic acid

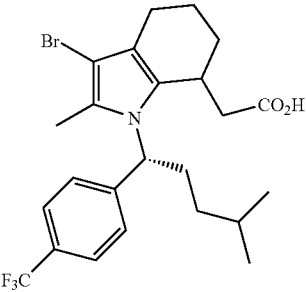

Step 1

To a stirred solution of Intermediate 3 (72 mg, 0.16 mmol) in dry THF (4 ml) at −78° C. was added NBS (34 mg, 0.19 mmol) as a solid. The resulting mixture was stirred at this temperature for 2 h, and then quenched with NaHCO₃(aq). The mixture was extracted with EtOAc (×2), the combined organic phases were dried (MgSO₄), and purified by flash chromatography (Biotage SP1, 12M, 0->8% EtOAc/isohexane) to give a pale yellow oil. (70 mg, 82%).

Step 2

The product of Step 1 (25 mg, 0.05 mmol), was dissolved in EtOH (3 mL), and 0.5M NaOH(aq) (0.29 mL) was added. After stirring at RT for 2 h, the solvent was removed under reduced pressure, and the residue was partitioned between 2M HCl (aq)/DCM, filtered through a phase-separation cartridge and concentrated. Purification by flash chromatography (Biotage SP1, 25S, 20->75% EtOAc/isohexane) gave a white foam, (15 mg, 63%). Mixture of diastereoisomers ¹H NMR (400 MHz), δ (ppm) (CDCl₃): 7.56 (2H, t), 7.14 (1H, d), 7.02 (1H, t), 5.22-5.16 (1H, m), 3.18 (1H, d), 2.52-2.0 (9H, m), 1.55-1.86 (5H, m), 1.37-1.17 (2H, m), 0.99-0.85 (6H, m); (ES⁺) 500, 502 (M+H⁺).

Example 2

(3-Chloro-2-methyl-1-{(1R)-4-methyl-1-[4-(trifluoromethyl)phenyl]pentyl}-4,5,6,7-tetrahydro-1H-indol-7-yl)acetic acid

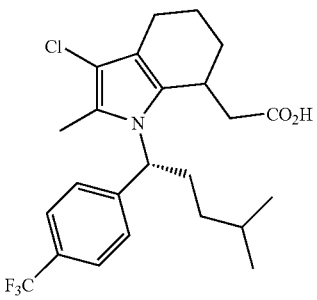

Prepared from Intermediate 3 and N-chlorosuccinimide using an analogous procedure to Example 1. ¹H NMR (500 MHz), δ (ppm) (CDCl₃): 7.56 (2H, t,), 7.14 (11H, d), 7.03 (1H, d), 5.20-5.14 (1H, m), 3.19 (1H, m), 2.57-2.33 (4H, m), 2.26-2.18 (1H, m), 2.14-2.01 (3H, s), 1.86-1.68 (6H, m), 1.38-1.19 (2H, m), 0.96-0.89 (6H, m); (ES⁺) 456, 458 (M+H⁺).

Example 3

(3-Benzoyl-2-methyl-1-{(1R)-4-methyl-1-[4-trifluoromethyl)phenyl]pentyl}-4,5,6,7-tetrahydro-H-indol-7-yl)acetic acid

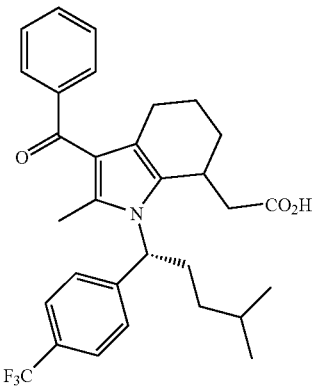

Step 1
To a stirred solution of Intermediate 3 (80 mg, 0.18 mmol) and benzoyl chloride (25 mg, 0.18 mmol) in DCM (3 mL) was added aluminium trichloride (24 mg, 0.18 mmol). The resulting wine-red solution was stirred at RT for 18 h, and then quenched with NaHCO₃(aq). The mixture was extracted with DCM, the combined organic phases were dried (sodium sulfate), concentrated under reduced pressure, and purified by flash chromatography (Biotage SP1, 12M 0->40% EtOAc/isohexane) to give a yellow oil (9 mg, 9%).
Step 2
Analogous procedure to Example 1, Step 2.
¹H NMR (400 MHz), δ (ppm) (CDCl₃): 7.68 (2H, d), 7.60 (2H, t), 7.51-7.39 (3H, m), 7.21-7.02 (2H, m), 5.30 (1H, m), 3.15-3.3 (1H, m), 2.56-1.36 (17H, m), 0.99-0.85 (6H, m); (ES⁺) 526 (M+H⁺).

Example 4

(3-Cyano-2-methyl-1-{(1R)-4-methyl-1-[4-trifluoromethyl)phenyl]pentyl}-4,5,6,7-tetrahydro-1H-indol-7-yl)acetic acid

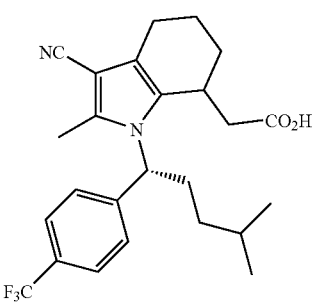

Step 1
To a stirred solution of the Intermediate 3 (72 mg, 0.16 mmol) in DMF (1 mL) at −78° C. was added chlorosulfonyl isocyanate (45 mg, 0.32 mmol) in acetonitrile (1 mL), and the resulting mixture was stirred at this temperature for 4 h, and then allowed to warm to RT over 4 h, and stir for a further 16 h. The mixture was quenched with NaHCO₃(aq), and extracted with DCM (×3), the combined organic phases were dried (sodium sulphate) and concentrated. Purification by flash chromatography (0->30% EtOAc/isohexane) gave a foam (12 mg, 16%).
Step 2
Analogous procedure to Example 1, Step 2.
¹H NMR (400 MHz), δ (ppm) (CDCl₃): δ 7.60 (2H, t), 7.10 (2H, dd), 5.27-5.21 (1H, m), 3.17 (1H, m), 2.65 (1H, m), 2.56-2.36 (3H, m), 2.23-2.04 (5H, m), 1.86-1.67 (4H, m), 1.35-1.09 (4H, m), 0.97-0.83 (6H, m); (ES⁺) 447 (M+H⁺).

Example 5

(3-Cyclohexyl-1-{(1R)-4-methyl-1-[4-(trifluoromethyl)phenyl]pentyl}-4,5,6,7-tetrahydro-1H-indol-7-yl)acetic acid

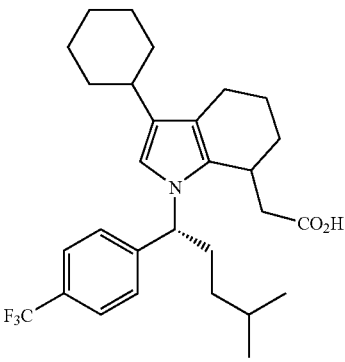

Step 1
Sodium hydride, 60% dispersion in oil (13.9 g, 34.8 mmol) was added portionwise to dimethoxyethane (300 mL) with water cooling. Triethyl phosphonoacetate (69 mL, 34.8 mmol) was added slowly. The mixture was stirred for 90 minutes at RT. Cyclohexanecarboxaldehyde (15 g, 13.4 mmol) was added and the mixture was stirred at RT for 18 h. Water (200 mL) was added and the mixture was extracted with ether. The organic phase was washed with brine, dried over sodium sulphate and concentrated to dryness. The residue was purified by column chromatography (40:1 isohexane-ethyl acetate) to give an oil (19.8 g, 79%).
¹H NMR (400 MHz), δ (ppm) (CDCl₃): 6.91 (1H, dd, J 6.7, 15.8), 5.76 (1H, dd, J 1.5, 15.8), 4.18 (2H, q, J 7.1), 2.16-2.10 (1H, m), 1.76 (4H, dd, J 3.0, 12.9), 1.69 (1H, d, J 1.3), 1.31-1.13 (8H, m).
Stet 2
DIBAH, 1M in hexanes (268 mL, 26.8 mmol) was added dropwise to a stirred solution of the product of Step 1 (19.5 g, 10.7 mmol) in ether (25 mL) maintaining the temperature below −70° C. The mixture was stirred at −78° C. for 3 h and then quenched with methanol followed by sat. ammonium chloride solution. The mixture was allowed to warm to RT, diluted with ether and washed with 2M HCl. The organic phase was washed with water and then brine, dried over sodium sulphate and concentrated to give a colourless oil (12.3 g, 82%). ¹H NMR (400 MHz), δ (ppm) (CDCl₃): 5.67-5.55 (2H, m), 4.08 (2H, m), 2.00-1.94 (1H, m), 1.70 (5H, m), 1.32-1.02 (6H, m).

Step 3

A few drops of propionic acid were added to the product of Step 2 (2.5 g, 17.9 mmol) and Intermediate 4 (8.4 g). The mixture was stirred and heated at 150° C. for 18 h then cooled to RT. The reaction mixture was purified directly by column chromatography (5->10% EtOAc/isohexane) to give an oil (703 mg, 13%) as a mixture of diastereomers.

Step 4

Nitrogen was bubbled into a stirred solution of the product of Step 3 (703 mg, 2.28 mmol) in DCM (40 mL) at −78° C. for a few minutes. Oxygen was then bubbled into the mixture followed by ozone. A blue colour persisted after a few minutes. Oxygen was bubbled through the mixture until the blue colour disappeared followed by nitrogen. Dimethylsulphide (1.0 mL, 13.7 mmol) was added and the mixture was stirred at −78° C. for 2 h and then allowed to warm to RT overnight. The mixture was concentrated to dryness. The residue was dissolved in EtOAc and washed with water and brine, dried over sodium sulphate and concentrated to dryness to afford the dicarbonyl compound as a complex mixture of diastereomeric ketals (774 mg).

Step 5

A mixture of product from Step 4 (774 mg, 2.51 mmol), Intermediate 2 (739 mg, 3.01 mmol), lithium perchlorate (266 mg, 2.51 mmol) and acetic acid (0.4 ml) in toluene (25 ml) was stirred and heated under reflux in a flask equipped with a Dean-Stark apparatus for 20 h. After cooling to RT and dilution with EtOAc, the mixture was washed with sat. NaHCO₃ solution and brine, dried over sodium sulphate and concentrated to dryness. The residue was purified by column chromatography (20:1 isohexane:EtOAc) to give an oil as a 1:1 mixture of diastereomers (398 mg, 31%). m/z (ES⁺) 518 (M+H⁺).

Step 6

A mixture of the product from Step 5 (398 mg, 0.768 mmol) and lithium hydroxide (184 mg, 7.68 mmol) in water (4 mL) and dioxane (30 mL) was stirred and heated under reflux for 18 h. After cooling to RT and acidification to pH 1 with 1M hydrochloric acid, the mixture was extracted with EtOAc and the organic extract was washed with water and brine, dried over sodium sulphate and concentrated to dryness. The residue was purified by column chromatography (0.5% acetic acid in 40:1 DCM:methanol) to give a pale brown foamy solid. The chromatographed material was separated into single diastereomers using preparative HPLC (HIRPB column 250×20 mm id, 85% MeCN and 15% TFA (0.1%) in water, 20 ml/min). The first eluted compound was designated diastereomer 1 (61 mg). ¹H NMR (500 MHz), δ (ppm) (CDCl₃): 7.49 (2H, d, J 8.2), 7.02 (2H, d, J 8.1), 6.53 (1H, s), 4.95 (1H, dd, J 6.2, 9.2), 2.93 (1H, m), 2.63-2.55 (2H, m), 2.49 (11H, m), 2.37-2.31 (2H, m), 2.17-2.09 (1H, m), 2.04-1.97 (1H, m), 1.93 (2H, m), 1.76-1.66 (8H, m), 1.40-1.30 (4H, m), 1.24-1.16 (3H, m), 0.88 (6H, t, J 6.1). The second eluted compound was designated diastereomer 2 (60 mg). ¹H NMR (500 MHz), δ (ppm) (CDCl₃): 7.55 (2H, d, J 8.2), 7.25 (2H, d, J 8.2), 6.50 (1H, s), 5.00 (11H, t, J 7.6), 3.29 (11H, m), 2.53 (11H, m), 2.44-2.36 (2H, m), 2.24 (1H, dd, J 11.1, 15.7), 2.09-2.01 (2H, m), 1.95 (3H, m), 1.81-1.51 (7H, m), 1.43-1.07 (8H, m), 0.88 (6H, m).

Examples 6-9

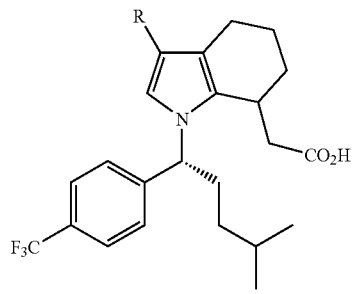

Examples 6-9 were made in analogous fashion to Example 5 starting from the appropriate aldehyde.

| Example No | R | m/z |
| --- | --- | --- |
| 6 | Neopentyl | ES⁻ (M − H⁺) 476 |
| 7 | Isopropyl | ES⁻ (M − H⁺) 448 |
| 8 | Cyclopentyl | ES⁺ (M + H⁺) 476 |
| 9 | Cyclobutyl | ES⁺ (M + H⁺) 462 |

Examples 10-11

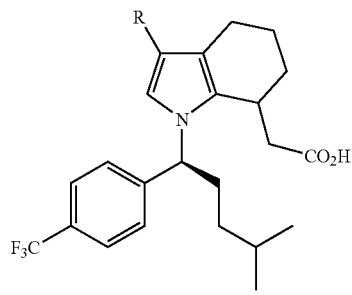

Examples 10-11 were made in analogous fashion to Example 5 starting from the appropriate aldehyde and using Intermediate 1 in Step 5 in place of Intermediate 2.

| Example No | R | m/z |
| --- | --- | --- |
| 10 | Cyclopentyl | ES⁺ (M + H⁺) 476 |
| 11 | Cyclobutyl | ES⁺ (M + H⁺) 462 |

Example 12

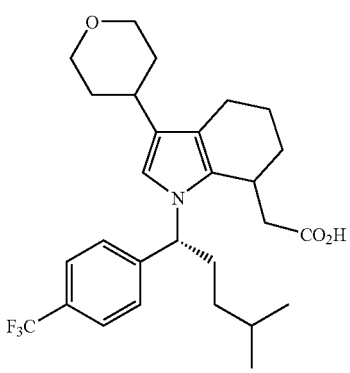

Step 1

3-Tetrahydro-2H-pyran-4-yl)prop-2-en-1-ol (prepared by the method of Example 5 Steps 1 and 2 starting with tetrahydropyran-4-carboxaldehyde) (2.16 g, 15.2 mmol) and cyclohexanone diethyl ketal (3.66 g, 21.3 mmol) containing a few drops of propionic acid were stirred and heated at 150° C. for 18 h. After cooling to RT, the mixture was purified by column chromatography (7:1->4:1 isohexane:EtOAc to give an oil as a mixture of diastereomers; 1.17 g (35%).

Step 2

A solution of the product from Step 1 (1.17 g, 5.27 mmol) in THF (5 mL) was added slowly to a solution of KHMDS, 0.5 M in hexanes (11.6 ml, 5.80 mmol) in THF (25 mL) at −78° C. maintaining the temperature below −70° C. The mixture was stirred at −78° C. for 1. Ethyl bromoacetate (641 μL, 5.80 mmol) was added dropwise, ensuring the temperature remained below −70° C. The mixture was stirred at −78° C. for 2 hours and allowed to warm to RT whereupon it was quenched with saturated ammonium chloride solution. The mixture was extracted with ethyl acetate. The organic phase was washed with brine, dried over sodium sulphate and concentrated to dryness. The residue was purified by column chromatography (4:1 isohexane:EtOAc) to give an oil 620 mg, (38%) as a mixture of diastereomers.

Step 3

The product of Step 2 was treated as in Example 5 Steps 4-6 to provide the title compound. m/z ES− (M−H+) 490.

Example 13

(3-Trifluoromethyl)-1-{(1R)-4-methyl-1-[4-trifluoromethyl)phenyl]pentyl}-4,5,6,7-tetrahydro-1H-indol-7-yl)acetic acid

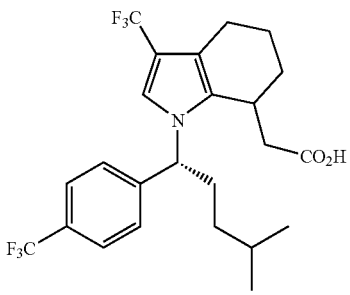

Prepared by the method of Example 12 using 4,4,4-trifluorobut-2-en-1-ol in Step 1. m/z ES− (M−H+) 474.

Example 14

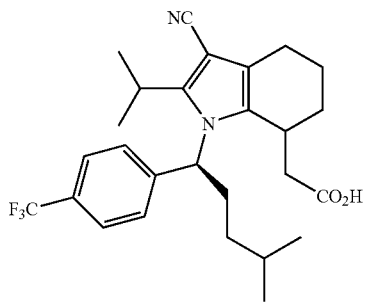

Step 1

Intermediate 4 was reacted with 2-isopropylprop-2-en-1-ol by the method of Example 5 Step 3 and the product oxidised with RuCl₃/NaIO₄ as described for Step 3 of Intermediate 3. Reaction of the resulting diketone with Intermediate 2 by the method of Example 5 Step 1 gave the ethyl ester of (2-isopropyl-1-{(1S)-4-methyl-1-[4-trifluoromethyl)phenyl]pentyl}-4,5,6,7-tetrahydro-1H-indol-7-yl)acetic acid.

Step 2

To a stirred solution of the product of Step 1 (1.0 g, 2.1 mmol) in DMF (8 mL) at −78° C. was added chlorosulfonyl isocyanate (0.2 ml, 2.1 mmol) in acetonitrile (8 mL). The resulting mixture was stirred at this temperature for 4 h, and then allowed to warm to room temperature over 4 h, and stirred for a further 16 h. The mixture was quenched with NaHCO₃(aq), and extracted with DCM (×3), the combined organic phases were dried (MgSO₄) and concentrated. Purification by flash chromatography (0->30% EtOAc/isohexane) gave a foam (720 mg, 65%).

Step 3

The product of Step 3 was hydrolysed as described in Example 1 Step 2. The product was purified by flash chromatography (SiO₂, 9:1->2:1 isohexane:EtOAc) to give the product as a mixture of diastereoisomers. The diastereoisomers were separated using reverse-phase preparative HPLC. First eluted compound (diastereoisomer 1) ¹H NMR δ (ppm) (CDCl₃): 7.59 (2H, d, J 8.2 Hz), 7.14 (2H, br), 5.17 (11H, br), 3.29 (11H, m), 2.66-2.49 (5H, m), 2.10 (2H, m), 1.77-1.23 (13H, m), 0.99 (3H, d, J 6.5 Hz), 0.93 (3H, d, J 6.5 Hz).

Second eluted compound (diastereoisomer 2) ¹H NMR δ (Ppm)(CDCl₃): 7.62 (2H, d, J 8.2 Hz), 7.22 (2H, d, J 8.2 Hz), 5.20 (1H, m), 3.28 (1H, br), 2.71-2.49 (5H, m), 2.10 (2H, m), 1.77-1.23 (13H, m), 0.99 (3H, d, J 6.5 Hz), 0.93 (3H, d, J 6.5 Hz).

Example 15

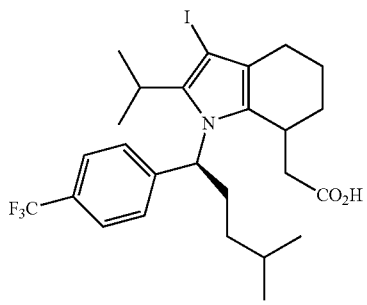

To a stirred solution of the product of Example 14 Step 1 (500 mg, 1.1 mmol) in dry THF (10 ml) at −20° C. was added N-iodosuccinimide (242 mg, 1.1 mmol). Reaction was slowly allowed to warm to room temperature and stirred for 2 h. The reaction was then quenched with NaHCO$_3$(aq) and then the product extracted with EtOAc (×3). The organics were washed with brine, dried (MgSO$_4$), filtered and evaporated. The residue was hydrolysed by the procedure of Example 1, Step 2 and purified by flash chromatography (SiO$_2$, 4:1->1:1 isohexane:EtOAc) to give the product as a mixture of diastereoisomers.

$^1$H NMR δ (ppm) (CDCl$_3$): 7.57 (2H, m), 7.25 (1H, m), 7.07 (1H, m), 5.12 (1H, br), 3.21 (1H, m), 2.60-0.85 (26H, m).

Example 16

(3-(1,1-Dimethylethyl)-1-{1-4-methyl-1-[4-(trifluoromethyl)phenyl]pentyl}-4,5,6,7-tetrahydro-1H-indazol-7-yl)acetic acid

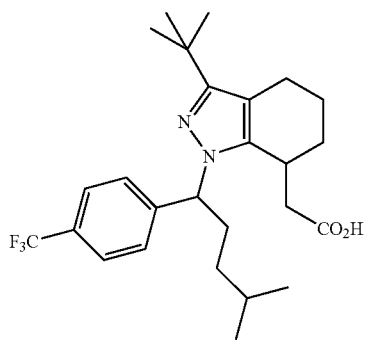

Step 1: 7-Allyl-3-(1,1-dimethylethyl)-4,5,6,7-tetrahydro-1H-indazole

A 1M solution of lithium hexamethyldisilazide in THF (40 mL, 0.04 mol) was added dropwise to solution of 2-allylcyclohexanone (5 g, 0.036 mol) in dry THF (50 mL) cooled below −70° under N$_2$. After 1 h, a solution of 1-(2,2,2-trimethylacetyl)-1H-benzotriazole (7.2 g, 0.036 mol) in dry THF (10 mL) was added in one portion and the mixture allowed to reach room temperature over 2 h. After a further 1 h, 1N hydrochloric acid (50 mL) was added and the mixture extracted with ether (3×50 mL). The combined organic phase was washed with 1N Na$_2$CO$_3$ solution (20 mL), brine (20 mL), dried (MgSO$_4$) and concentrated to an oil. TLC silica (EtOAc:Hexane 10%) showed three products A, B and C (Rf, 0.6, 0.25 and 0.2 respectively). MPLC on silica eluting with EtOAc:Hexane 00->20% enabled isolation of 3 g of A, an oil, 1.5 g of B and 0.7 g of C. NMR showed A to be the O-acylated material and B and C the desired diastereomeric products, cis- and trans-2-allyl-6-(1-(2,2,2-trimethylacetyl))cyclohexan-1-one.

$^1$H NMR δ (ppm) (CDCl$_3$): A; 5.85-5.65 (1H, m), 5.35-5.3 (1H, m), 5.05-4.95 (2H, m), 2.5-1.4 (9H, m), 1.25 (s, 9H): B; 5.85-5.65 (1H, m), 5.05-4.95 (2H, m), 4.15-4.05 (1H, m), 2.8-1.3 (9H, m), 1.14 (s, 9H): C; 5.85-5.65 (1H, m), 5.05-4.95 (2H, m), 3.95-3.85 (1H, m), 2.6-1.3 (9H, m), 1.10 (s, 9H).

Combined fractions B and C (1.9 g) was dissolved in ethanol (20 mL), hydrazine hydrate (2 mL) was added and the resulting solution was stirred at RT for 2 h. The mixture was concentrated and the residue dissolved in ether (50 mL). The solution was washed with 1N hydrochloric acid (10 mL), dried (MgSO$_4$) and re-concentrated to give 7-allyl-3-(1,1-dimethylethyl)-4,5,6,7-tetrahydro-1H-indazole as a gum, 1.8 g.

$^1$H NMR δ (ppm) (CDCl$_3$): 5.9-5.75 (1H, m), 5.15-5.05 (2H, m), 3.15-2.85 (2H, m), 2.5-2.7 (2H, m), 2.5-2.35 (1H, m), 1.95-1.85 (2H, m), 1.75-1.5 (2H, m), 1.45 (9H, m).

Step 2:

Sodium hydride 60% dispersed in oil (0.4 g, 0.01 mol) was added portionwise to a solution of 7-allyl-3-(1,1-dimethylethyl)-4,5,6,7-tetrahydro-1H-indazole [Step 1] (1.8 g, 0.082 mol) in dry DMF stirring at rt. After 30 min, Intermediate 5 (3 g, 0.01 mol) was added and the mixture stirred at room temperature for 18 h. The mixture was partitioned between ether (100 mL and water (50 mL). The organic phase was separated, dried (MgSO$_4$), and concentrated to an oil which was purified by MPLC on silica with EtOAc:Hexane 0->10% as eluant to give 1.5 g of 7-allyl-3-(1,1-dimethylethyl)-1-{1-(4-methyl-1-[4-(trifluoromethyl)phenyl]pentyl)}-4,5,6,7-tetrahydro-1H-indazole as an oil.

Step 3:

RuCl$_3$ hydrate (15 mg) was added to mixture of 7-allyl-3-(1,1-dimethylethyl)-1-{1-(4-methyl-1-[4-(trifluoromethyl)phenyl]pentyl)}-4,5,6,7-tetrahydro-H-indazole [Step 2] (1 g, 0.002 mol) and sodium periodate (1.7 g, 0.008 mol) in a mixture of CCl$_4$ (4 mL), CH$_3$CN (4 mL) and water (6 mL) stirring rapidly at room temperature. After 24 h the mixture was partitioned between water (10 mL) and DCM (3×50 mL). The organic phase was concentrated and the residue purified by MPLC on silica with DCM:MeOH 0->10% as eluant followed by RP HPLC on a C-18 column eluting with 70% CH$_3$CN:0.1% TFAaq. as eluant to give (3-(1,1-dimethylethyl)1-{1-(4-methyl-1-[4-(trifluoromethyl)phenyl]pentyl)}-4,5,6,7-tetrahydro-1H-indazol-7-yl)acetic acid as a 1:1 mixture of diastereomers. MS ES(M+1), 465. $^1$H NMR δ (ppm) (CDCl$_3$): 7.56-7.51 (2H of Diast A+1H of Diast B), 7.37, (1H Diast B, d, J=8 Hz), 4.95-5.05 (1H A+1H B, m), 3.4-3.3 (1H A, m), 3.1-3.2 (1H B, m), 2.7-1.4 (13H A+B, m), 1.33 and 1.31 (9H A+B, 2s), 0.88 and 0.84 (6H A+B, d, J=6 Hz).

Example 17

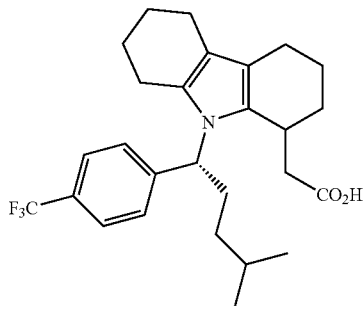

Step 1:

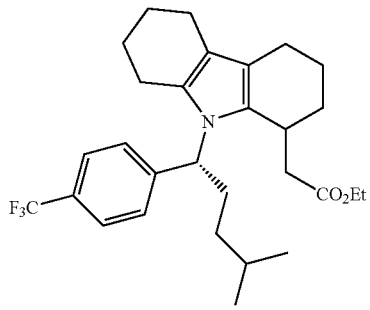

Prepared according to the method of Intermediate 3 using 1-cyclohexene-1-methanol in Step 1; m/z ES⁺ (M+H⁺) 490.

Step 2

Step 1 was converted to the corresponding acid according to the method for Example 5, step 6. m/z ES⁺ (M+H⁺) 462.

Example 18

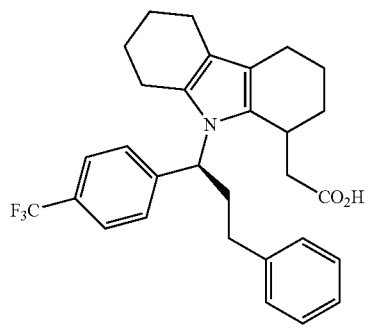

Step 1

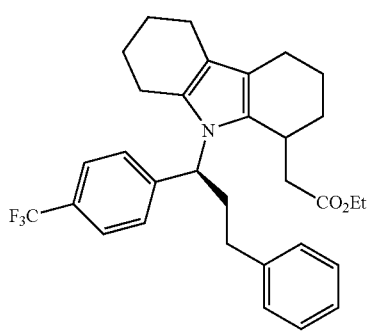

Prepared using the method of Intermediate 3 using 1-cyclohexene-1-methanol in Step 1 and Intermediate 7 in step 4; m/z ES⁺ (M+H⁺) 524.

Step 2

Step 1 was converted to the corresponding acid according to the method for example 5, step 6. m/z ES⁺ (M+H⁺) 496.

Examples 19-22

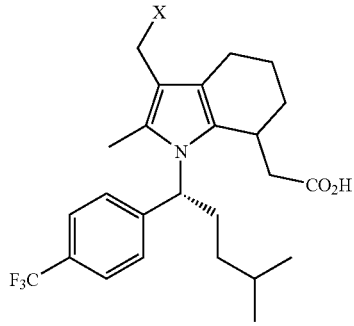

Prepared according to the following typical procedure (X=morpholine):

Step 1

To a stirred solution of the Intermediate 6 (60 mg, 0.13 mmol) and morpholine (11 mg, 0.13 mmol) in chloroform (3 ml) was added sodium triacetoxyborohydride (82 mg, 0.39 mmol) and the resulting mixture was stirred at room temperature for 16 h. The mixture was quenched with sat. NaHCO₃ (aq), and filtered through a phase-separation cartridge, washing with DCM. Concentration under reduced pressure gave the crude ester as a colourless oil, which was taken on crude to step 2.

Step 2

Step 1 was converted to the corresponding acid according to the method for example 5, step 6. ¹H NMR (400 MHz, CDCl₃): δ 7.54 (d, 2 H), 7.16 (t, 2 H), 5.23 (m, 1 H), 3.70 (t, 4 H), 3.42 (s, 2 H), 3.22 (d, 1 H), 2.53-0.70 (m, 26 H) m/z ES⁺ (M+H⁺) 507.

| Example No | X | m/z |
|---|---|---|
| 19 | Morpholine | ES⁺ (M + H⁺) 507 |
| 20 | Aniline | ES⁺ (M + H⁺) 513 |
| 21 | Benzylamine | ES⁺ (M + H⁺) 527 |
| 22 | 4-Phenylpiperazine | ES⁺ (M + H⁺) 582 |

Example 23

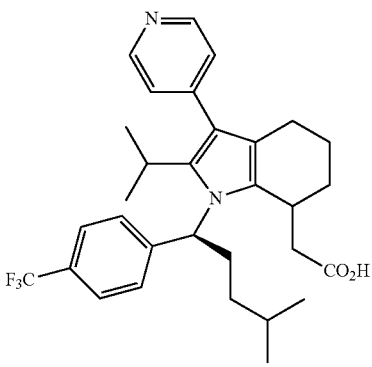

To the iodide from Example 15 (320 mg, 0.54 mmol) in dioxane (4 ml) were added pyridine-4-boronic acid (100 mg, 0.81 mmol), bis(diphenylphosphino)ferrocene dichloropalladium(II) (20 mg, 5 mol %) and 2M Na₂CO₃ (aq). The mixture was subjected to microwave radiation to heat at 170° C. for 15 min. Reaction was diluted with water and extracted with EtOAc (×3). The organic extracts were washed with brine, dried (magnesium sulfate), filtered and evaporated. The residue was purified by flash chromatography (SiO$_2$, 9:1 DCM/MeOH to 5:1 DCM/MeOH) to give a white solid as mix of diastereoisomers. $^1$H NMR δ (ppm) (CDCl$_3$): 8.53 (2H, br), 7.60 (2H, d, J=8.0 Hz), 7.27 (4H, m), 5.27 (1H, br), 3.39 (1H, br), 2.61-0.87 (20H, m).

m/z (ES) 527 (MH$^+$).

Examples 24-38

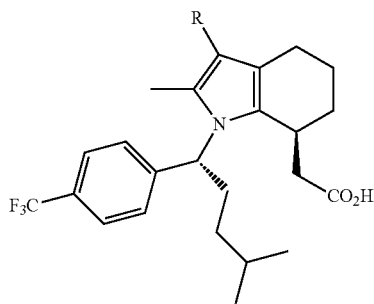

Step 1

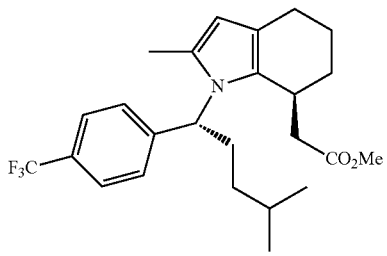

(a) To a stirred solution of Intermediate 3 (28.1 g, 66.7 mmol) in dry THF (300 ml) cooled to 0° C. was added triethylamine (18.6 ml, 133 mmol) followed by trimethylacetyl chloride (9.8 ml, 80 mmol). The resulting mixture was stirred for 10 min, prior to addition of a mixture of (S)-5-benzyl-2-oxazolidinone (14.19, 80 mmol) and lithium chloride (8.03 g, 189 mmol) as a solid. Stirring was continued for a further 16 h, before solvent removal under reduced pressure. The residue was partitioned between water and ethyl acetate, and the aqueous phase was extracted (3× ethyl acetate). The combined organic phases were washed (brine), dried (sodium sulfate) and concentrated under reduced pressure to give an oil, which was purified by flash chromatography (Biotage SPI system, gradient elution from 3-30% diethyl ether/isohexane). The top eluting diastereoisomer was isolated as a white solid (15.5 g, 40%) was taken on to the next step.

(b) To a stirred solution of the oxazolidinone (10.4 g, 17.9 mmol) in (3:1) THF-water (100 ml) was added lithium hydroxide monohydrate (1.5 g, 35.8 mmol), and the resulting mixture was stirred at room temperature for 16 h. The solvent was removed under reduced pressure and the residue was partitioned between 2M HCl (aq) and EtOAc. The aqueous phase was extracted with EtOAc, the combined organic phases were washed (brine), dried (sodium sulfate) and concentrated under reduced pressure to give an oil, which was dissolved in DMF (50 ml). Potassium carbonate (7.43 g, 53.7 mmol) followed by iodomethane (3.35 ml, 53.7 mmol) was added and the mixture was heated to 40° C. for 16 h. The mixture was filtered, and the filtrate was concentrated under reduced pressure to give an oil, which was partitioned between EtOAc and water. The aqueous phase was extracted with EtOAc, the combined organic phases were washed (brine), dried (sodium sulfate) and concentrated under reduced pressure to give an oil which was purified by flash chromatography (Biotage SPI, gradient elution from 2-20% EtOAc/isohexane to give a colourless oil (4.0 g, 51%). $^1$H NMR (400 MHz, CDCl$_3$): δ 7.55 (d, 2 H), 7.14 (d, 2 H), 5.72 (s, 1 H), 5.21 (dd, 1 H), 3.60 (s, 3 H), 3.23 (d, 1 H), 2.55-2.31 (m, 4 H), 2.21-2.03 (m, 2 H), 1.87 (s, 3 H), 1.76 (br, 4 H), 1.30-1.24 (m, 2 H), 1.02 (t, 1 H), 0.94-0.86 (m, 6 H). m/z (ES$^+$) 436 (M+H$^+$).

Step 2(a)

The product of Step 1 was treated with NBS as described in Example 1 Step 1 to provide the 3-bromo derivative. $^1$H NMR (400 MHz, CDCl$_3$): δ 7.57 (d, 2 H), 7.16 (t, 2 H), 5.23 (dd, 1 H), 3.60 (d, 3 H), 3.24 (d, 1 H), 2.54-2.32 (m, 4 H), 2.20-2.04 (m, 3 H), 1.85-1.73 (m, 6 H), 1.27-1.19 (m, 2 H), 0.98-0.90 (m, 7 H).

Alternative Step 2(b)

The product of Step 1 was treated with N-iodosuccinimide as in Example 15 to provide the 3-iodo derivative. $^1$H NMR (500 MHz, CDCl$_3$): δ 7.57 (d, 2 H), 7.14 (d, 2 H), 5.25 (dd, 1 H), 3.59 (s, 3 H), 3.23 (d, 1 H), 2.49-2.27 (m, 4 H), 2.19-2.04 (m, 2 H), 1.89 (s, 3 H), 1.82-1.65 (m, 2 H), 1.63-1.51 (m, 1 H) 1.36-1.20 (m, 2 H), 0.97-0.83 (m, 8 H).

Step 3

The product from Step 2(b) (0.162 mmol), 4-trifluoromethyl)benzeneboronic acid (46 mg, 0.243 mmol), Pd(dppf) Cl$_2$ (5.9 mg, 0.008 mmol) and 2M sodium carbonate solution (324 μl, 0.694 mmol) in dioxane (2 ml) were stirred and heated at 100° C. for 18 hours. The mixture was allowed to cool to room temperature and then concentrated to dryness. The crude residue and lithium hydroxide (44 mg, 1.91 mmol) in 5:1 dioxane-water (2 ml) were stirred and heated at 100° C. for 18 hours. The mixture was cooled to room temperature and concentrated to dryness. The residue was diluted with DCM (2 ml) and water (2 ml) and adjusted to pH 5/6 with dilute hydrochloric acid. The organic phase was separated using a phase separation cartridge and concentrated to dryness. The residue was dissolved in DMSO (1 ml) and Example 24 was isolated using mass-directed preparative HPLC.

Using this method, and employing Step 2(a) or 2(b) as indicated, the following were prepared.

| Example | Step 2 | R group | m/z (ES$^+$) (M + H$^+$) |
|---|---|---|---|
| 24 | (b) | 4-(Trifluoromethyl)phenyl | 566 |
| 25 | (b) | 2,4-Difluorophenyl | 534 |
| 26 | (b) | 4-Chlorophenyl | 533 |
| 27 | (b) | 4-(Trifluoromethoxy)phenyl | 582 |
| 28 | (b) | 2,4-Dichlorophenyl | 567 |
| 29 | (b) | 2-(Trifluoromethyl)phenyl | 566 |
| 30 | (b) | 3,4-Dichlorophenyl | 567 |
| 31 | (b) | 2,3-Dichlorophenyl | 567 |
| 32 | (b) | 2,5-Difluorophenyl | 534 |
| 33 | (b) | 2,5-Dichlorophenyl | 567 |
| 34 | (a) | 5-Indolyl | 537 |
| 35 | (a) | 6-Quinolyl | 549 |
| 36 | (a) | 7-Thiophenyl | 554 |

-continued

| Example | Step 2 | R group | m/z (ES+) (M + H+) |
|---|---|---|---|
| 37 | (a) | 5-Pyrimidinyl | 500 |
| 38 | (a) | 4-Pyrazolyl | 488 |

Examples 39-47

Following procedure similar to those described for Example 5-13, the following were also prepared:

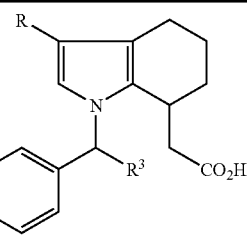

| Example | R | $R^3$ |
|---|---|---|
| 39 | cyclohexyl | 2-(3,4-difluorophenyl)ethyl |
| 40 | cyclohexyl | 2-(3-trifluoromethylphenyl)ethyl |
| 41 | cyclohexyl | 2-(4-pyridyl)ethyl |
| 42 | cyclopentyl | 2-phenylethyl |
| 43 | cyclopentyl | 2-(morpholin-4-yl)ethyl |
| 44 | cyclopentyl | 2-(4-pyridyl)ethyl |
| 45 | cyclopentyl | 2-(3,4-difluorophenyl)ethyl |
| 46 | cyclopentyl | 3-methylbut-3-en-1-yl |
| 47 | cyclopentyl | 2-(2-pyridyl)ethyl |

Glossary
KHMDS—potassium hexamethyldisilazide
DCM—dichloromethane
THF—tetrahydrofuran
DMF—dimethylformamide
RT—room temperature
DIBAH—diisobutylaluminium hydride
TFA—trifluoroacetic acid
EtOAc—ethyl acetate
EtOH—ethanol
$Et_2O$—diethyl ether
NBS—N-bromosuccinimide

The invention claimed is:

1. A compound of formula I:

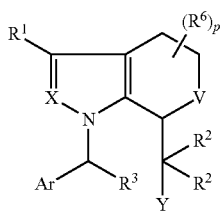

(I)

wherein V represents a bond, $CH_2$ or $CH_2CH_2$;
X represents $CR^{1a}$;
Y represents $CO_2H$ or tetrazole;
Ar represents phenyl which optionally bears up to 3 substituents independently selected from hydrocarbon groups of up to 6 carbon atoms and $(CH_2)_m$—Z where m is 0, 1 or 2 and Z represents halogen, $N_3$, CN, $CF_3$, $OCF_3$ or $OR^4$;
$R^1$ represents Cl, Br, I, CN, or $R^4CO$;
$R^{1a}$ represents H or $C_{1-4}$alkyl;
each $R^2$ is independently H or $C_{1-4}$alkyl;
$R^3$ is H, hydrocarbon containing up to 10 carbon atoms, benzyloxy$C_{1-4}$alkyl or heterocyclyl$C_{1-4}$alkyl, any of which optionally bears up to 3 substitutents selected from halogen and $CF_3$, or 1 substituent selected from $C_{1-4}$alkoxy and $C_{1-4}$alkylthio, wherein heterocyclyl refers to aromatic or nonaromatic rings of 5 or 6 atoms of which 1, 2 or 3 atoms are selected from N, O and S;
$R^4$ represents H or a hydrocarbon group of up to 7 carbon atoms, optionally substituted with halogen, CN, $CF_3$, OH, $C_{1-4}$alkoxy or $C_{1-4}$alkoxycarbonyl;
$R^5$ represents $R^4$ that is other than H;
p is 0, 1 or 2; and
$R^6$ represents $C_{1-6}$alkyl, $C_{2-6}$alkenyl or phenyl, benzyl or heteroaryl, said phenyl, benzyl or heteroaryl optionally bearing up to 3 substituents selected from halogen, CN, $CF_3$, $OCF_3$, $OR^4$, $CO_2R^4$, $COR^4$, $OCOR^5$ and $C_{1-4}$alkyl;
or a pharmaceutically acceptable salt thereof.

2. A compound of formula I:

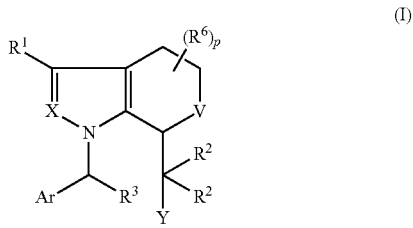

(I)

wherein V represents a bond, $CH_2$ or $CH_2CH_2$;
X represents $CR^{1a}$;
Y represents $CO_2H$ or tetrazole;
Ar represents phenyl which optionally bears up to 3 substituents independently selected from hydrocarbon groups of up to 6 carbon atoms and $(CH_2)_m$—Z where m is 0, 1 or 2 and Z represents halogen, $N_3$, CN, $CF_3$, $OCF_3$ or $OR^4$;
$R^1$ represents halogen, CN, or $R^4CO$;
$R^{1a}$ represents $C_{1-4}$alkyl;
each $R^2$ is independently H or $C_{1-4}$alkyl;
$R^3$ is H, hydrocarbon containing up to 10 carbon atoms, benzyloxy$C_{1-4}$alkyl or heterocyclyl$C_{1-4}$alkyl, any of which optionally bears up to 3 substitutents selected from halogen and $CF_3$, or 1 substituent selected from $C_{1-4}$alkoxy and $C_{1-4}$alkylthio, wherein heterocyclyl refers to aromatic or nonaromatic rings of 5 or 6 atoms of which 1, 2 or 3 atoms are selected from N, O and S;
$R^4$ represents H or a hydrocarbon group of up to 7 carbon atoms, optionally substituted with halogen, CN, $CF_3$, OH, $C_{1-4}$alkoxy or $C_{1-4}$alkoxycarbonyl;
$R^5$ represents $R^4$ that is other than H;
p is 0, 1 or 2; and
$R^6$ represents $C_{1-6}$alkyl, $C_{2-6}$alkenyl or phenyl, benzyl or heteroaryl, said phenyl, benzyl or heteroaryl optionally bearing up to 3 substituents selected from halogen, CN, $CF_3$, $OCF_3$, $OR^4$, $CO_2R^4$, $COR^4$, $OCOR^5$ and $C_{1-4}$alkyl;
or a pharmaceutically acceptable salt thereof.

3. A compound of formula I:

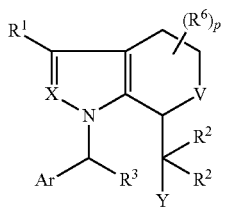

wherein V represents a bond, $CH_2$ or $CH_2CH_2$;
X represents $CR^{1a}$;
Y represents $CO_2H$ or tetrazole;
Ar represents phenyl which optionally bears up to 3 substituents independently selected from hydrocarbon groups of up to 6 carbon atoms and $(CH_2)_m$—Z where m is 0, 1 or 2 and Z represents halogen, $N_3$, CN, $CF_3$, $OCF_3$ or $OR^4$;
$R^1$ and $R^{1a}$ complete a fused cycloalkene ring of 5, 6 or 7 members which is optionally substituted with up to 2 $C_{1-4}$alkyl groups;
each $R^2$ is independently H or $C_{1-4}$alkyl;
$R^3$ is H, hydrocarbon containing up to 10 carbon atoms, benzyloxy$C_{1-4}$alkyl or heterocyclyl$C_{1-4}$alkyl, any of which optionally bears up to 3 substitutents selected from halogen and $CF_3$, or 1 substituent selected from $C_{1-4}$alkoxy and $C_{1-4}$alkylthio, where "heterocyclyl" refers to aromatic or nonaromatic rings of 5 or 6 atoms of which 1, 2 or 3 atoms are selected from N, O and S;
$R^4$ represents H or a hydrocarbon group of up to 7 carbon atoms, optionally substituted with halogen, CN, $CF_3$, OH, $C_{1-4}$alkoxy or $C_{1-4}$alkoxycarbonyl;
$R^5$ represents $R^4$ that is other than H;
p is 0, 1 or 2; and
$R^6$ represents $C_{1-6}$alkyl, $C_{2-6}$alkenyl or phenyl, benzyl or heteroaryl, said phenyl, benzyl or heteroaryl optionally bearing up to 3 substituents selected from halogen, CN, $CF_3$, $OCF_3$, $OR^4$, $CO_2R^4$, $COR^4$, $OCOR^5$ and $C_{1-4}$alkyl;
or a pharmaceutically acceptable salt thereof.

4. A pharmaceutical composition comprising a compound according to claim 1 or a pharmaceutically acceptable salt thereof and a pharmaceutically acceptable carrier.

5. A pharmaceutical composition comprising a compound according to claim 2 or a pharmaceutically acceptable salt thereof and a pharmaceutically acceptable carrier.

6. A pharmaceutical composition comprising a compound according to claim 3 or a pharmaceutically acceptable salt thereof and a pharmaceutically acceptable carrier.

* * * * *